(12) United States Patent
Hayakawa et al.

(10) Patent No.: US 10,779,779 B2
(45) Date of Patent: Sep. 22, 2020

(54) PORTABLE RADIATION IMAGING APPARATUS

(71) Applicant: SHIMADZU CORPORATION, Kyoto (JP)

(72) Inventors: Toru Hayakawa, Kyoto (JP); Hajime Takemoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 90 days.

(21) Appl. No.: 16/012,822

(22) Filed: Jun. 20, 2018

(65) Prior Publication Data

US 2019/0059837 A1 Feb. 28, 2019

(30) Foreign Application Priority Data

Aug. 25, 2017 (JP) .................................. 2017-161774

(51) Int. Cl.
*A61B 6/00* (2006.01)
*A61B 6/06* (2006.01)

(52) U.S. Cl.
CPC .............. *A61B 6/4405* (2013.01); *A61B 6/06* (2013.01); *A61B 6/447* (2013.01); *A61B 6/485* (2013.01); *A61B 6/461* (2013.01); *A61B 6/467* (2013.01)

(58) Field of Classification Search
CPC ......... A61B 6/4405; A61B 6/06; A61B 6/447; A61B 6/485; A61B 6/461; A61B 6/467
See application file for complete search history.

(56) References Cited

U.S. PATENT DOCUMENTS

| | | | | |
|---|---|---|---|---|
| 4,223,222 A | * | 9/1980 | Gray | A61B 6/447 250/363.08 |
| 4,335,315 A | * | 6/1982 | Waerve | A61B 6/4429 248/281.11 |
| 4,461,367 A | * | 7/1984 | Eichinger | B60K 7/0007 180/252 |
| 4,752,948 A | * | 6/1988 | MacMahon | A61B 6/4405 378/193 |
| 5,325,413 A | * | 6/1994 | Habraken | A61B 6/4283 378/181 |
| 5,351,282 A | * | 9/1994 | Kadowaki | A61B 6/4405 378/193 |

(Continued)

FOREIGN PATENT DOCUMENTS

JP 4014282 9/1999

*Primary Examiner* — Blake C Riddick
(74) *Attorney, Agent, or Firm* — Andrew F. Young, Esq.; Lackenbach Siegel, LLP (57) ABSTRACT

A portable radiation imaging apparatus improves visibility while moving by arranging the supporting column in the low-position. A base 46 is at a bottom end of a supporting column 41 and is fixed to turntable 78. A surface holding bearing 60 has an inner ring 61 and an outer ring 62 between the turntable 78 and a bottom plate 79. The inner ring 61 of the surface holding bearing 60 is fixed to the turntable 78 and the outer ring 62 is fixed to the bottom plate 79. The turntable 78 revolves with the supporting column 41 around the revolving center C, as the center, of the supporting column 41 and the turntable 78. An idler element 65 has a first circumference 63 and a second circumference 64 is installed to a circumference of the surface holding bearing 60. The revolving-side stopper 81 and the fixing-side stopper 82 regulate the idler element 65.

3 Claims, 8 Drawing Sheets

(56) References Cited

U.S. PATENT DOCUMENTS

| | | | | |
|---|---|---|---|---|
| 5,499,284 | A | * | 3/1996 | Pellegrino ............ A61B 6/4405 378/197 |
| 5,506,883 | A | * | 4/1996 | Exner .................. A61B 6/4405 378/197 |
| 5,784,435 | A | | 7/1998 | Figurski |
| 6,215,846 | B1 | * | 4/2001 | Mazess ................ A61B 6/4225 348/E3.045 |
| 2005/0135565 | A1 | * | 6/2005 | Boomgaarden ...... A61B 6/4429 378/193 |
| 2006/0065846 | A1 | * | 3/2006 | Ertel .................... G01T 1/2018 250/370.11 |
| 2007/0014116 | A1 | * | 1/2007 | Yoshimori .............. B60Q 7/00 362/386 |
| 2008/0123819 | A1 | * | 5/2008 | Jensen ................. A61B 6/4405 378/198 |
| 2011/0123001 | A1 | * | 5/2011 | Kopcienski .......... A61B 6/4405 378/198 |
| 2013/0188781 | A1 | * | 7/2013 | Kaku ................... A61B 6/4405 378/197 |
| 2015/0177100 | A1 | * | 6/2015 | Dietz .................... F03D 17/00 702/182 |
| 2015/0300404 | A1 | * | 10/2015 | Frank .................... F16C 35/04 384/510 |
| 2016/0199013 | A1 | * | 7/2016 | Moreno Vallejo ... A61B 6/4405 378/194 |
| 2017/0236679 | A1 | * | 8/2017 | Chaki ................... H01J 35/26 378/131 |

* cited by examiner

PORTABLE RADIATION IMAGING APPARATUS

CROSS REFERENCE TO RELATED APPLICATIONS

This application relates to, and claims priority from, JP 2017-161774 filed Aug. 25, 2017, the entire contents of which are incorporated herein by reference.

FIGURE SELECTED FOR PUBLICATION

FIG. 4

BACKGROUND OF THE INVENTION

Field of the Invention

The present invention relates to a portable radiation imaging apparatus.

Description of the Related Art

A portable radiation imaging apparatus that is a type of such portable radiation imaging apparatus is also called the visiting X-ray imaging apparatus that carries out the X-ray imaging in the patient room from one to another. Such portable X-ray imaging apparatus comprises a main body having front wheels and rear wheels, a supporting column standing on the main body, a lifting member that moves up-and-down along the supporting column while supporting an X-ray irradiation element comprising an X-ray tube and a collimator, an X-ray detector that detects the X-ray that the X-ray irradiation element irradiates and transmits through a subject, and a battery that is installed inside the main body.

With respect to such portable X-ray imaging apparatus, the lifting member supporting the X-ray irradiation element revolves 270-degrees clockwise around the supporting column as the center therefor relative to the main body, or e.g., revolves 270-degrees counterclockwise, so that the X-ray irradiation element can be positioned in an arbitrary location. Patent Document 1 discloses the portable X-ray imaging apparatus that comprises a pair of bearings that is in-place at which each is distant from another in the vertical direction and supports the supporting column to be revolvable, and a stopper mechanism that is in-place above the pair of the bearings and regulates the revolving angle location of the lifting member.

Further, Patent Document 2 discloses the portable X-ray imaging apparatus that comprises a revolving plate and a pair of revolving reference points, and further comprises the mechanism that regulates the revolving angle location of the arm in both a clockwise direction and counterclockwise direction.

RELATED PRIOR ART DOCUMENTS

Patent Document

Patent Document 1: JP Patent 4014282 B1
Patent Document 2: U.S. Pat. No. 5,784,435 Specification

ASPECTS AND SUMMARY OF THE INVENTION

Objects to be Solved

With respect to such portable X-ray imaging apparatus, it is preferable that the top of the supporting column is as low as possible so that the operator can improve the own front view when the operator moving the apparatus from the patient room to another. Particularly, with regard to the portable X-ray imaging apparatus having the multi steps lifting mechanism in which the lifting member is in-place above the top end of the supporting column when the lifting member is in-place in the climbing position, the top end of the supporting column can be in-place in the low-position, so that the supporting column should be in-place in further lower position so that the front of the apparatus can be recognized from the higher position than the top end of the supporting column.

In contrast, as disclosed in Patent Document 1, when the portable X-ray imaging apparatus comprises the pair of bearings that are in-place at which each is distant from another in the vertical direction and support the supporting column to be revolvable and a stopper mechanism that is in-place above the pair of the bearings and regulates the revolving angle location of the lifting member, the stopper mechanism is installed to further above location than the pair of bearings that are in-place distant from another in the vertical direction, so that the space in between such components is larger and as a result, it is problematic that the position of the supporting column is in the high-position.

The purpose of the present invention is to solve the above objects and to provide a portable radiation imaging apparatus that can improve visibility of the front thereof while moving by constituting the revolving mechanism of the supporting column and the regulation mechanism of the revolving angle location to be compact and arranging the supporting column in the low-position.

Means for Solving the Problem

According to one aspect of the claimed invention, a portable radiation imaging apparatus comprises a main body having wheels, a supporting column standing on the main body, a lifting member that moves up-and-down along the supporting column while holding a radiation irradiation element, and the portable radiation imaging apparatus further comprises a circular surface holding bearing, of which external diameter has the radius R1 from the revolving center of the supporting column, that is installed underneath the supporting column, supports the supporting column that can revolve around the center that is an axis that is the vertical axis relative to the main body, an idler element that is installed to a circumference of the surface holding bearing comprises a circular hole having a radius R2 that is longer than the radius R1 from the revolving center of the supporting column, a first circular circumference having an external diameter that has a radius R3, from the revolving center of said supporting column, that is longer than said radius R2 and a circular second circumference having an external diameter that has a radius R4, from the revolving center of the supporting column, that is longer than the radius R3, a revolving-side stopper that is connected with the supporting column so that the revolving stopper revolves along with the supporting column thereby is installed to a first location that is distant in a first distance that is longer than the radius R3 from the revolving center of the supporting column and shorter than the radius R4 from the revolving center of the supporting column, and a fixing-side stopper that is fixed to the main body at a second location that is distant in a second distance that is longer than the radius R3 from the revolving center of the supporting column and shorter than the radius R4.

The surface holding bearing of the second invention, according to one aspect of the above claimed invention, is a cross-roller bearing or a swing bearing.

According to one aspect of the above claimed invention, the lifting member is in-place in the higher position than the top end of the supporting column when the lifting member is in-place in the climbing position.

Effect of the Invention

According to one aspect of the above claimed invention, the revolving mechanism of the supporting column and the regulation mechanism of the revolving angle location are structured to be compact and the supporting column is arranged in the low-position, so that the front visibility can be improved while moving.

According to one further aspect of the above claimed invention, the location of the supporting column can be arranged in the lower position.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, an 'operation appartus' or 'imaging apparatus' or 'operation unit' or device etc., structure or feature etc. in this field will be understood to be well understood by those of skill in the art, which is understood to be understood to a very high skill in the art with a great deal of pre-existing technical sophistication, understanding, training, engineering, computer, and scientific knowledge including each of Applicant's other published patent applications for similar Radiation Imaging Devices, to include the enabling internal radiation features, circuits, and structures necessary to function as described without having to identify anew every input/output element, display, lever, memory element, processing-circuit, storage feature, trigger, rail, switch, wire, plug, processing unit, display screen, etc. etc. and/or wherein any computer code resident in a memory will physically cause the processor to change and to read-in data via an input device (e.g., including via a radiation imaging apparatus, touch screen, toggle-lever etc.), process data within the processor or processors (plural) and output processed data via an output output device such as a viewing image screen or display which is changed to show the output image generated.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents (resistors, capacitors, transistors, heat sinks, links, switches etc.) noted herein and structures that accomplish the functions without restrictive language or label requirements since those of skill in the art are well versed in related radiation fluoroscopy imaging apparatus and devices, computer and operational controls and technologies of radiographic devices and all their sub components, including various circuits and combinations of circuits without departing from the scope and spirit of the present invention.

Although only a few embodiments have been disclosed in detail, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Figure 1:
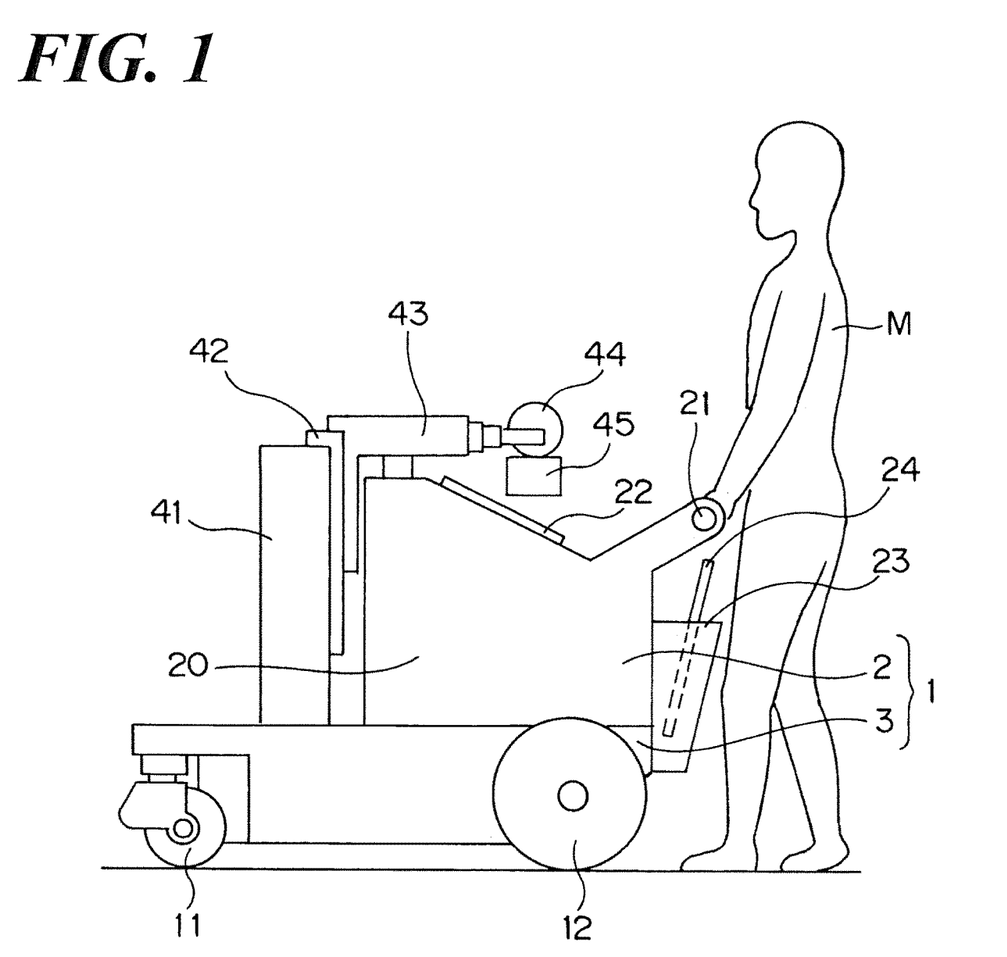
FIG. 1 is a schematic view illustrating a portable X-ray imaging apparatus as a portable radiation imaging apparatus according to the present invention.
Figure 2:
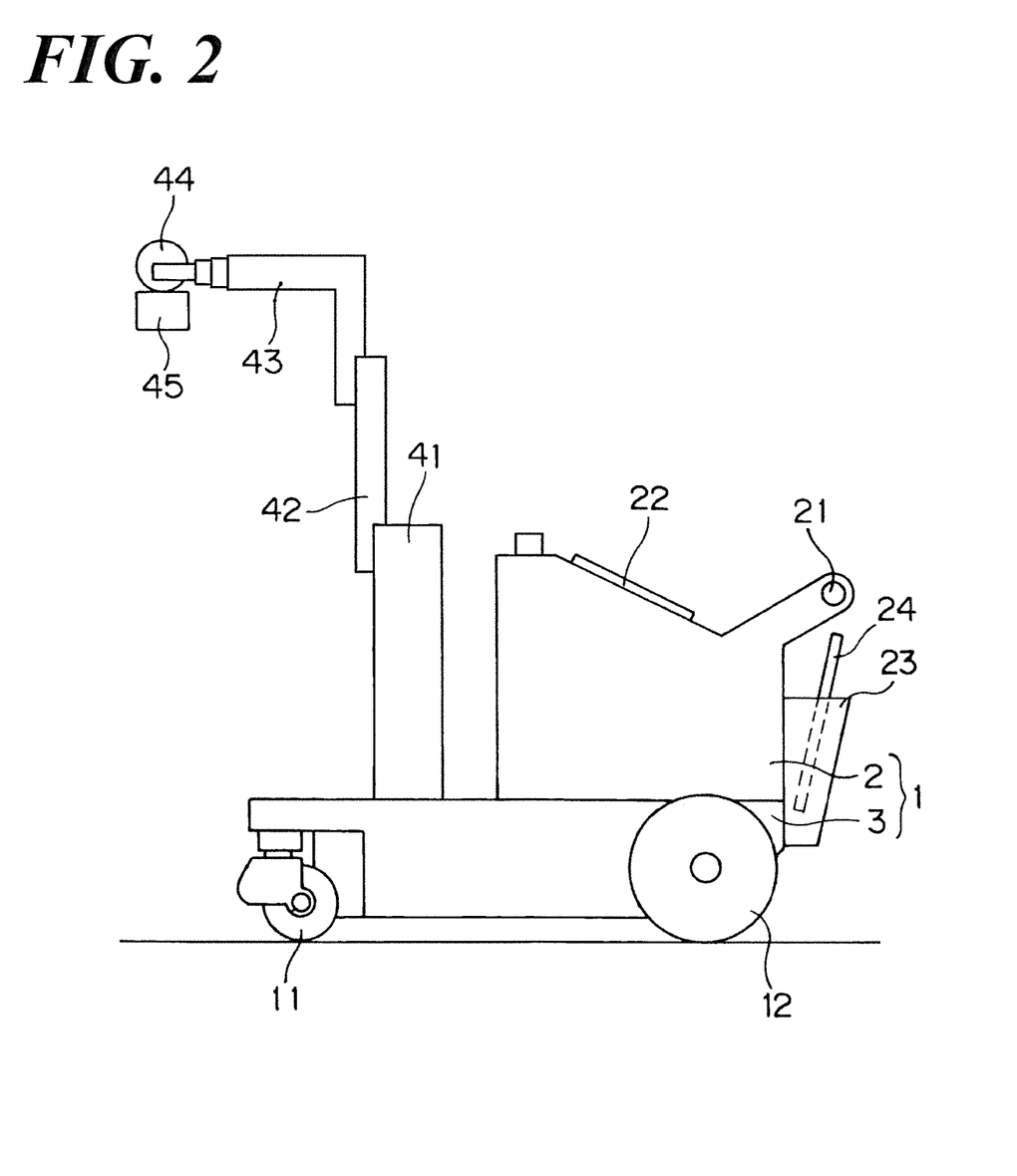
FIG. 2 is a schematic view illustrating a portable radiation imaging apparatus as a portable radiation imaging apparatus according to the present invention.

*The inventor sets forth Embodiments of the present invention based on the following FIGs. FIG. 1 and FIG. 2 are schematic views illustrating the portable X-ray imaging apparatus as the portable radiation imaging apparatus according to the present invention. In addition, FIG. 1 is illustrating the state of the portable X-ray imaging apparatus in the moving position and the FIG. 2 is illustrating the state of the portable X-ray imaging apparatus in the imaging position.

Such portable radiation imaging apparatus is also called a visiting X-ray imaging apparatus that carries out the X-ray imaging in the patient room from one to another in order and comprises the main body 1 having the body 2 and the chassis 3. A pair of right-and-left front wheels 11 that is for changing the direction is installed in the front-side relative to the traveling direction of the chassis 3 of such portable X-ray imaging apparatus. In addition, a pair of right-and-left rear wheels 12 that is for driving is installed in the back-side relative to the traveling direction of the chassis 3 of such portable X-ray imaging apparatus.

The supporting column 41 is installed in the standing position in the front-side relative to the traveling direction of the chassis 3, which constitutes the main body 1, and the first lifting member 42 and the second lifting member 43 are installed to the supporting column 41 and movable up-and-down. The second lifting member 43 has the approximately L-shape relative to the side view, and an X-ray irradiation element comprising an X-ray tube 44 and a collimator 45 is installed at the top end thereof. The first lifting member 42 and the second lifting member 43 constitutes the lifting member of the aspect of the present invention, and the X-ray tube 44 and the collimator 45 moves up-and-down along with the lifting operation of the first lifting member 42 and the second lifting member 43. In addition, the supporting column 41 is supported to be revolvable around the vertical axis, and the X-ray tube 44 and the collimator 45 gyrates along with the second lifting member 43 along with the revolving of the supporting column 41.

The body 2 that constitutes the main body 1 comprises an operation handle (lever) 21 that is operative to operate the traveling direction of the main body 1, an LCD touch-panel 22 that is operative as the display element and the operation element, and a housing 23 that houses such as an X-ray detector 24, such a flat panel detector and so forth, that detects the X-ray that is irradiated from the X-ray tube 44 and transmits through the subject.

Figure 3:
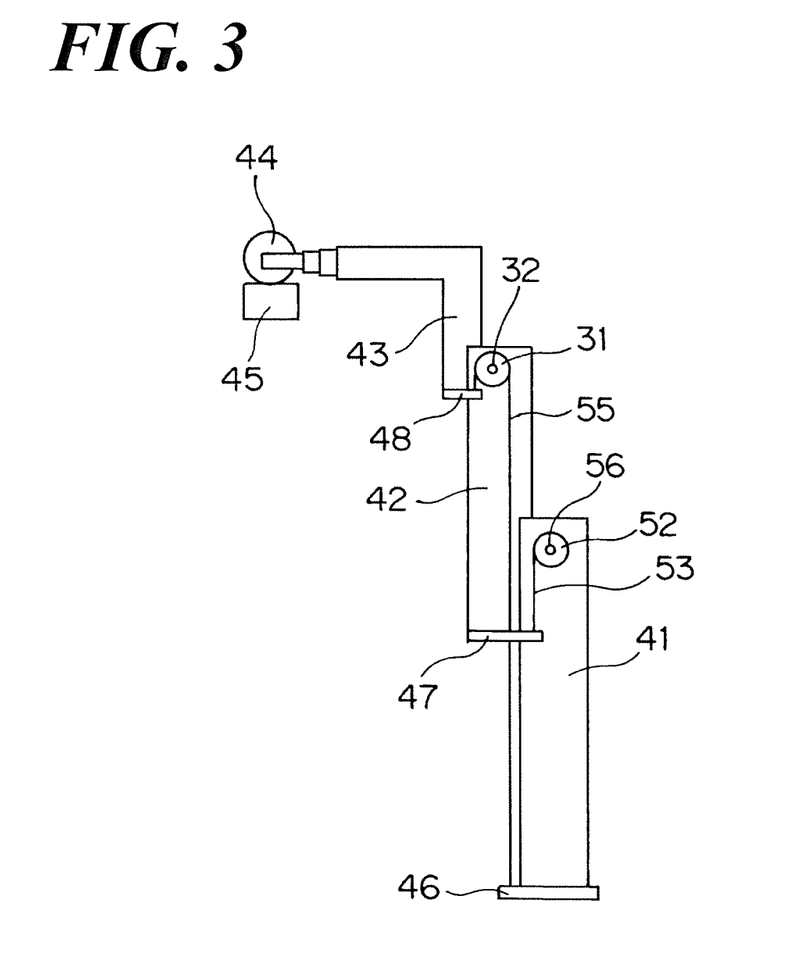
FIG. 3 is a schematic side view illustrating the lifting mechanism of the first lifting member 42 and the second lifting member 43.

The inventors set forth the lifting mechanism of the first lifting member 42 and the second lifting member 43. FIG. 3 is a schematic side view illustrating the lifting mechanism of the first lifting member 42 and the second lifting member 43.

The first lifting member 42 is movable up-and-down along the supporting column 41 according to a guide member, not shown in FIG., that is installed to the supporting column 41. In addition, the second lifting member 43 is movable up-and-down along the first lifting member 42 together with the X-ray tube 44 and the collimator 45 according to a guide member, not shown in FIG., that is installed to the first lifting member 42.

A winding pulley 52 is fixed on the upper portion of the supporting column 41 and revolvable around the first axis 56, which is fixed on the upper portion of the supporting column 41, as the center. And the one end of the second wire-rope 53 is fixed to the winding pulley 52, of which the other end is winded to the winding pulley 52, is fixed to the base 47 arranged to the bottom end of the first lifting member 42. Therefore, a winding amount of the wire-rope 53 relative to the winding pulley 52 varies depending on the revolving of the wining pulley 52, so that the first lifting member 42 moves up-and-down.

On the other hand, a fixed pulley 31 is fixed on the upper portion of the first lifting member 42 and revolvable around the second axis 32, which is fixed on the upper portion of the first lifting member 42, as the center. And the one end of the lifting first wire-rope 55 of the second lifting member 43, which is fixed to the base 46 arranged to the bottom end of the supporting column 41 and the other end thereof that is winded to the fixed pulley 31, is fixed to the base 48 arranged to the bottom end of the second lifting member 43. Therefore, the second wire-rope 53 is operative to lift the first lifting member, so that the second lifting member 43 also rises relative to the first lifting member 42 when the first wire-rope 55 rewinds toward the base 46. On the other hand, the second lifting member 43 also lowers relative to the first lifting member 42 when the first wire-rope 55 rewinds toward the base 48 by that the first lifting member 42 lowers.

Therefore, when the winding pulley 52 revolves so that the first lifting member 42 lifts, the second lifting member 43 lifts twice as the lifting amount of the first lifting member 42 along with the X-ray irradiation element comprising the X-ray tube 44 and the collimator 45. Therefore, when the winding pulley 52 revolves so that the first lifting member 42 lowers, the second lifting member 43 lowers twice as the downing amount of the first lifting member 42 along with the X-ray irradiation element comprising the X-ray tube 44 and the collimator 45. The operator M executes manually such lifting operation. The lifting assist mechanism, not shown in FIG., that assists such lifting operation is embedded inside the supporting column 41.

According to such structure, when the supporting column 41 revolves around the axis, as the center, vertically to the chassis 3 that constitutes the main body 1, the X-ray irradiation element comprising the X-ray tube 44 and the collimator 45 revolve together with the first lifting member 42 and the second lifting member 43.

Figure 4:
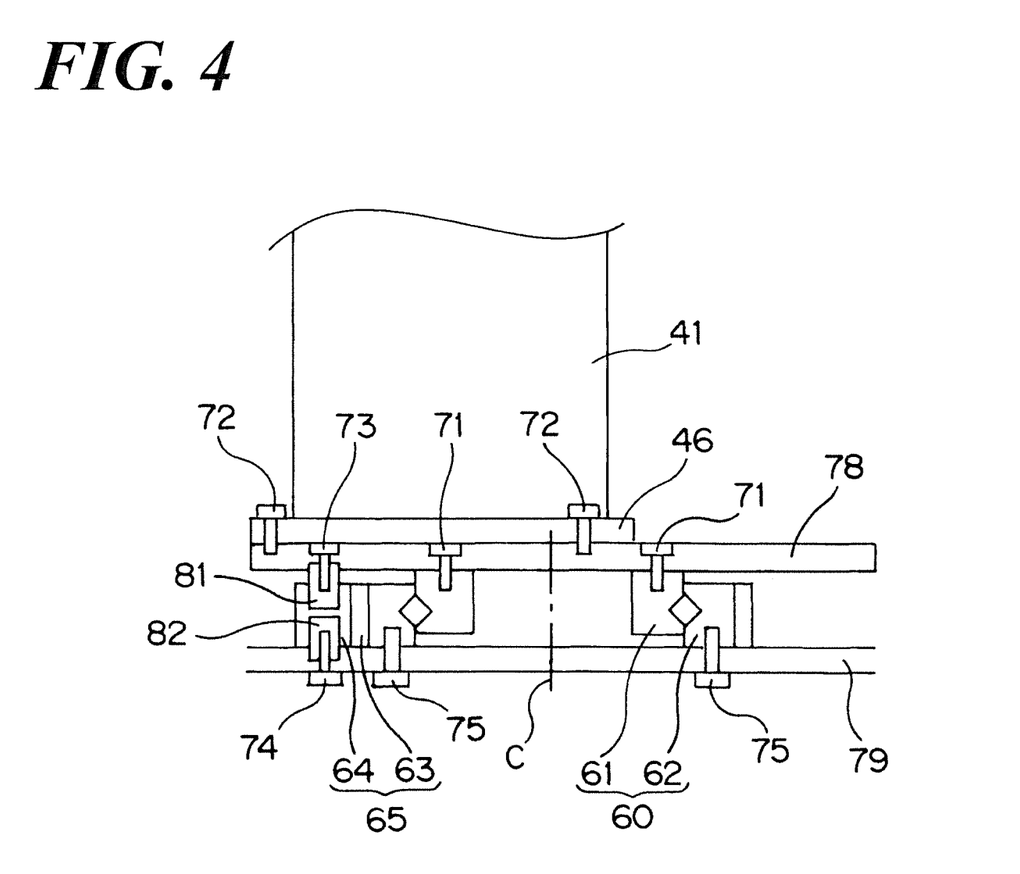
FIG. 4 is a vertical cross section view illustrating the revolving mechanism of the supporting column 41 installed underneath the supporting column 41 the regulation mechanism of the revolving angle location thereof.
Figure 5:
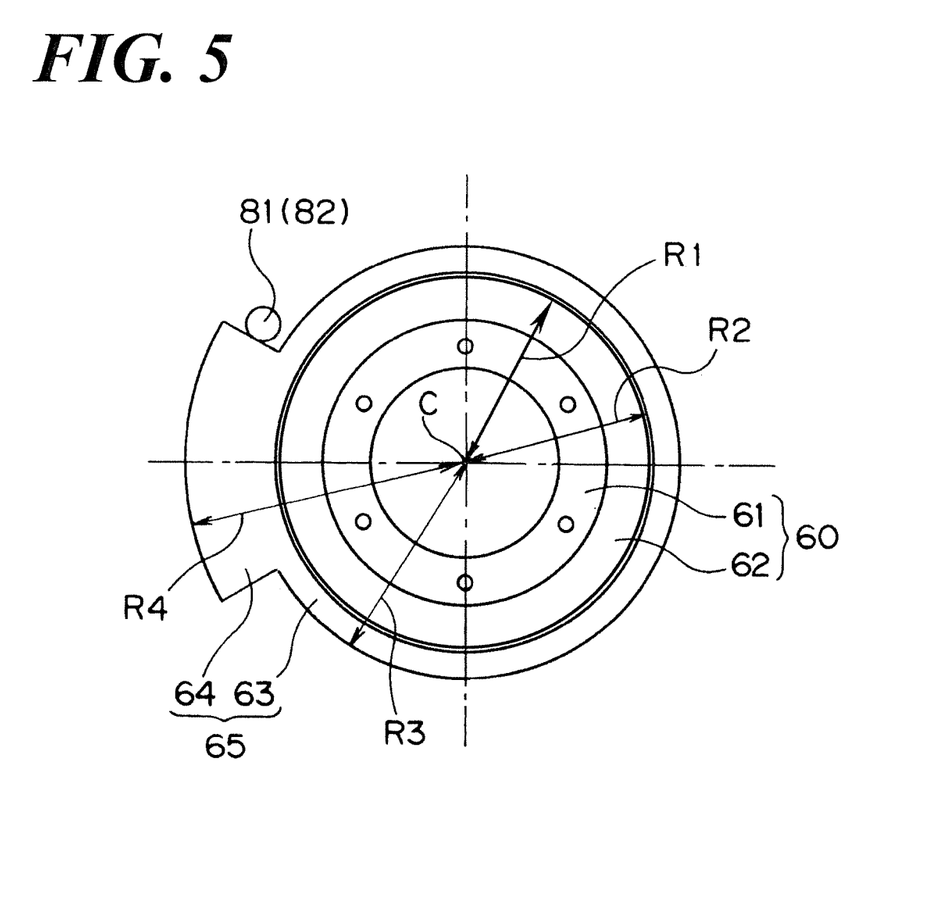
FIG. 5 is a plan view illustrating the main portions of the revolving mechanism of the supporting column 41 and the regulation mechanism of the revolving angle location thereof.

Hereinafter, the inventors set forth the feature of the present invention to carry out the revolving operation. FIG. 4 is a vertical cross section view illustrating the revolving mechanism of the supporting column 41 and the regulation mechanism of the revolving angle location, which are arranged underneath the supporting column 41. FIG. 5 is a plan view illustrating a principal portion of the revolving mechanism and the regulation mechanism of the revolving angle location of the supporting column 41.

Referring to FIG. 4, the base 46 that is installed to the bottom end of the supporting column 41, as set forth above, is fixed to the turntable 78 with a screw 72. The surface holding bearing 60 having the inner ring 61 and the outer ring 62 are installed between the turntable 78 and the bottom plate 79 of the above described chassis 3.

Such surface holding bearing 60 is the bearing that is operative to hold the moment, including the thrust load and the radial load, with the surface by the single bearing mechanism. Relative to such surface holding bearing 60, e.g., a cross-roller bearing, in which skids are alternatively arranged on the rolling surface having V-shape grooves formed in both inner ring and outer ring in the orthogonal direction, can be applied.

In addition, relative to the surface holding bearing 60, the revolving bearing angular thrust ball bearing structure in which four points contact takes place, The inner ring 61 of the surface holding bearing 60 are fixed to the turntable 78 with a plurality of screws 71. The outer ring 62 of the surface holding bearing 60 are fixed to the bottom plate 79 of the chassis 3 with a plurality of screws 75. Therefore, referring to FIG. 4, the turntable 78 revolves around the revolving center C, as the center, of the supporting column 41 and the turntable 78 indicated by the dashed line.

Referring to FIGS. 4, 5, an idler element 65 having the first circumference 63 and the second circumference 64 is installed to the circumference of the surface holding bearing 60. Such idler element 65 is a ring having a circular hole at the center thereof. And such idler element 65 revolves around the revolving center C, as the center, of the supporting column and the turntable 78 along the circumference of the surface holding bearing 60.

Referring to FIG. 5, the outer shape of the surface holding bearing 60 is a circularity having the radius R1 from the center that is the revolving center C of the supporting column 41 and the turntable 78. And the hole formed in the idler element 65 is the circularity having the radius R2 that is slightly longer than the radius R1 from the center that is the revolving center C of the supporting column 41 and the turntable 78. Therefore, the idler element 65 slides along the circumference of the surface holding bearing 60. In addition, the external diameter of the first circumference 63 relative to the idler element 65 is the circularity having the radius R3 that is longer than the radius R2 from the center that is the revolving center of the supporting column 41 and the turntable 78, and the external diameter of the second circumference 64 is the circularity having the radius R4 that is longer than the radius R3 from the center that is the revolving center C of the supporting column 41 and the turntable 78.

The revolving-side stopper 81 is fixed to the bottom surface of the turntable 78 that connects with the supporting column 41. Such revolving-side stopper 81 is in-place in the location distant in the distance shorter than the R4 and longer than R3 from the revolving center C of the supporting column 41 and the turntable 78. Therefore, such revolving-side stopper 81 is in-place in the location outside the first circumference 63 relative to the idler element 65 and in a contactable location to the side surface of the second circumference 64. And the revolving-side stopper 81 revolves together with the supporting column 41 and the turntable 78.

The fixing-side stopper 82 is fixed to the top surface of the bottom plate of the chassis 3 with the screw 74. Such fixing-side stopper 82 is in-place in the location distant in the distance shorter than the R4 and longer than R3 from the revolving center C of the supporting column 41 and the turntable 78. Therefore, such fixing-side stopper 82 is in-place in the location outside the first circumference 63 relative to the idler element 65 and in the contactable location to the side surface of the second circumference 64.

Figure 6A:
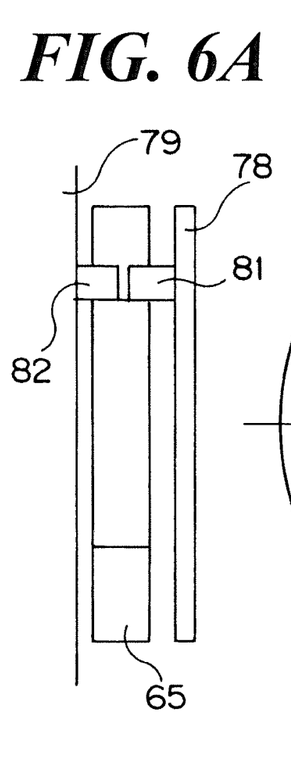
FIGS. 6A, 6B are explanatory views illustrating a regulation operation of the revolving angle location of the supporting column 41.
Figure 7:
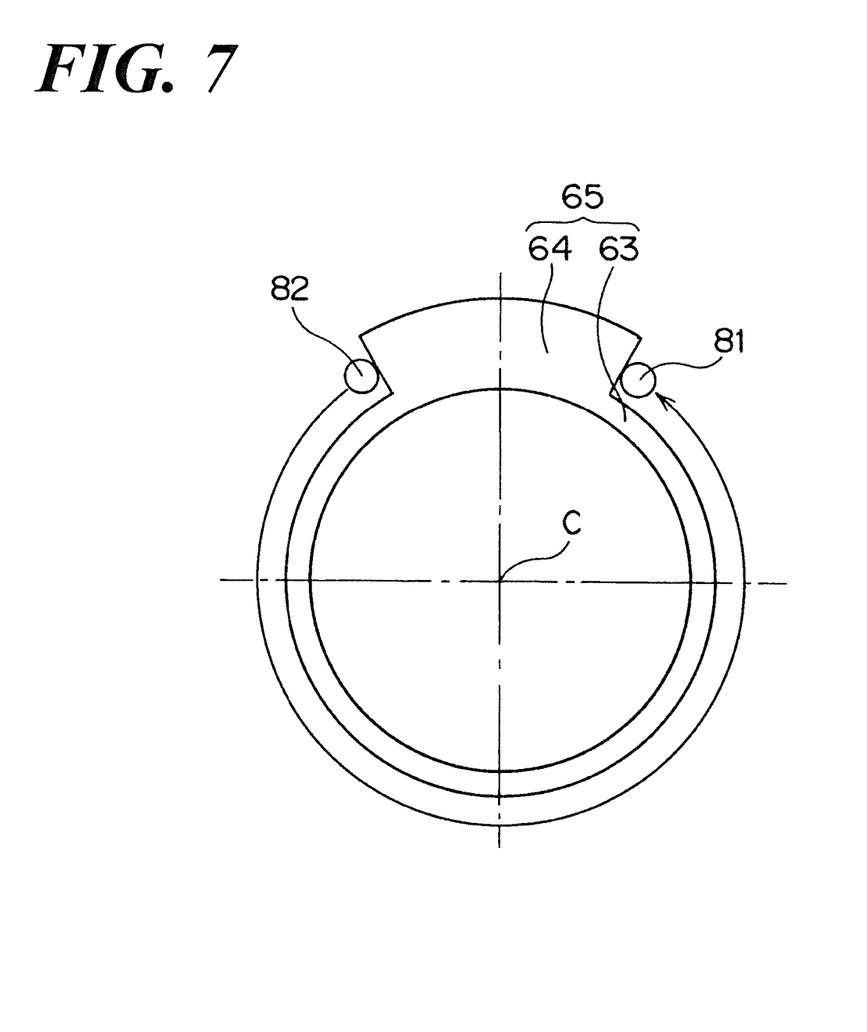
FIG. 7 is an explanatory view illustrating a regulation operation of the revolving angle location of the supporting column 41.
Figure 8:
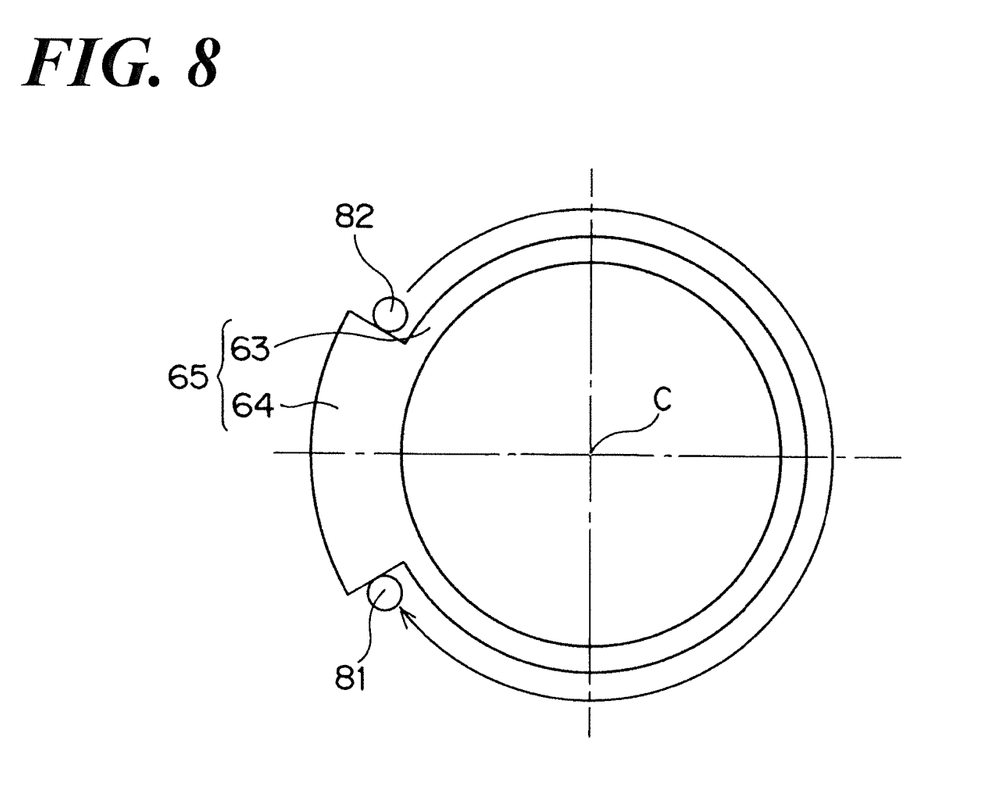
FIG. 8 is an explanatory view illustrating a regulation operation of the revolving angle location of the supporting column 41.

Next, the inventors set forth the regulation operation of the revolving angle location of the supporting column 41. FIG. 6A-FIG. 8 are the explanatory views illustrating the regulation operation of the revolving angle location of the supporting column 41. In addition, FIG. 6A is illustrating the side view of the idler element 65 and the revolving stopper 81, and FIG. 6B is illustrating the plan view thereof, and FIG. 7, FIG. 8 are illustrating each plan view of the idler element 65, the revolving-side stopper 81 and the fixing-side stopper 82.

Figure 6B:
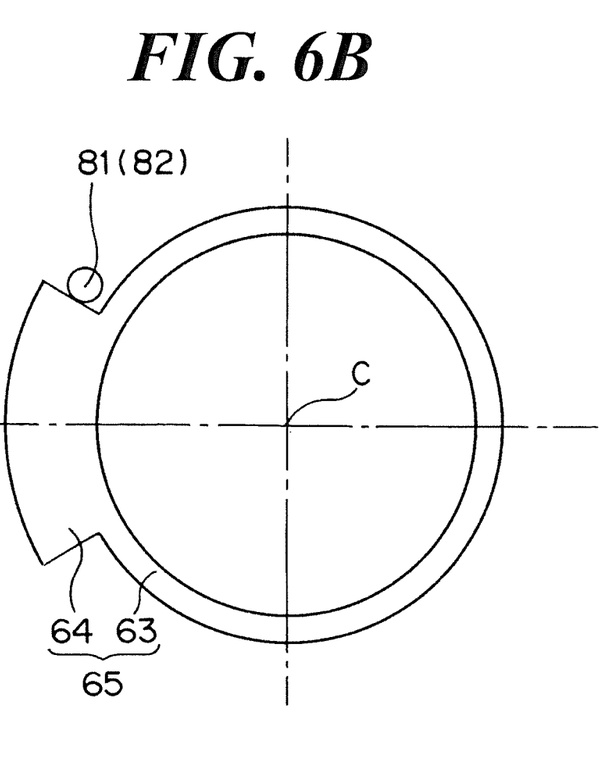

Referring additionally to FIGS. 6A, 6B, the second lifting member 43 is in the imaging position facing the front relative to the traveling direction as indicated in FIG. 2, FIG. 3. Therefore, in the above state, such revolving-side stopper 81 and the fixing-side stopper 82 contact with the side surface of the one side of the second circumference 64 relative to the idler element 65.

When the supporting column 41 turns counterclockwise indicated in FIGS. 6A, 6B and FIG. 7 with the turntable 78 from the above state, the revolving-side stopper 81 turns together with the turntable 78. At such state, the revolving-side stopper 81 presses the one side surface of the second circumference 64 relative to the idler element 65, so that the idler element 65 and the turntable 78 revolve together with each other in the same direction. And, referring to FIG. 7, when the other side of the second circumference 64 of the idler element 65 contacts with the fixing-side stopper 82, each revolving of the idler element 65 and the turntable 78 is regulated. At the above state, the angle between the line connecting the revolving center C of the supporting column 41 and the turntable 78 and the axis center of the revolving-side stopper 81 and the line connecting the revolving center C of the supporting column 41 and the turntable 78 and the axis center of the fixing-side stopper 82 is 90-degrees, the supporting column 41 and the turntable 78 together with the idler element 65 revolve 270-degrees counterclockwise from the state indicated in FIG. 6 to the state indicated in FIG. 7.

On the other hand, when the supporting column 41 turns clockwise indicated in FIGS. 6A, 6B and FIG. 8 with the turntable 78 from the state indicated in FIGS. 6A, 6B and FIG. 8, the revolving-side stopper 81 turns together with the turntable 78. At the above state, the idler element 65 does not turn. And, referring to FIG. 8, when the other side of the second circumference 64 of the idler element 65 contacts with the fixing-side stopper 82, each revolving of the idler element 65 and the turntable 78 is regulated. Even at the above state, the supporting column 41 and the turntable 78 turns clockwise 270-degrees from the state indicated in FIG. 6B and to the state indicated in FIG. 8.

Referring to FIG. 1, when moving the portable X-ray imaging apparatus having the above structure, the X-ray irradiation element comprising the X-ray tube 44 and the collimator 45 and the second lifting member 43, which are in-place in the top portion of the main body, are lowered in the moving position. Then, the operator grips the operation handle 21 and moves the portable X-ray imaging apparatus to the location where the operator carries out the X-ray imaging. As set forth above, at the above state, the revolving mechanism of the supporting column 41 and the regulation mechanism of the revolving angle location are in-place in the same plane area, so that the height position of the supporting column 41 can be kept in the low state. Therefore, the supporting column 41 does not block the eyesight of the operator M, so that the operator can visually recognize the front side in the traveling direction.

On the other hand, referring to FIG. 3, when the operator performs the X-ray imaging, the operator lifts the first lifting member 42 and the second lifting member 43 by using the lifting mechanism. And the operator revolves 270-degrees the support column 41 together with the X-ray irradiation element either clockwise or counterclockwise by using the revolving mechanism and the regulation mechanism of the revolving angle location. Accordingly, the operator can achieve the X-ray imaging at any required location.

Referring to FIG. 7, when the other side of the second circumference 64 of the idler element 65 contacts with the fixing-side stopper 82, each revolving of the idler element 65 and the turntable 78 is regulated. At the above state, the angle between the line connecting the revolving center C of the supporting column 41 and the turntable 78 and the axis center of the revolving-side stopper 81 and the line connecting the revolving center C of the supporting column 41 and the turntable 78 and the axis center of the fixing-side stopper 82 is 90-degrees, the supporting column 41 and the turntable 78 together with the idler element 65 revolve 270-degrees counterclockwise from the state indicated in FIG. 6B to the state indicated in FIG. 7. At the above state, the angle between the line connecting the revolving center C of the supporting column 41 and the turntable 78 and the axis center of the revolving-side stopper 81 and the line connecting the revolving center C of the supporting column 41 and the turntable 78 and the axis center of the fixing-side stopper 82 can be other than 90-degrees. At the above state, the supporting column 41 and the turntable 78 turn any degrees other than 270-degrees together with the idler element 65.

In addition, according to the aspect of the above described Embodiment, the first lifting member 42 and the second lifting member 43 lift relative to the supporting column 41, but the single lifting member can be lifted.

In addition, an image intensifier (I. I.) can be applied as the X-ray detector 24 other than the flat panel detector, or a sheet (detector) using such as an X-ray film and a photostimulable phosphor can be applied.

REFERENCE OF SIGNS

1 Main body
2 Body
3 Chassis
11 Front wheel
12 Rear wheel
31 Fixed pulley
24 X-ray detector
41 Supporting column
42 First lifting mechanism
43 Second lifting mechanism
44 X-ray tube
45 Collimator
52 Winding pulley
53 Second wire-rope
60 Surface holding bearing
61 Inner ring
62 Outer ring
63 First circumference
64 Second circumference
65 Idler element
78 Turntable
79 Bottom plate
81 Revolving-side stopper
82 Fixing-side stopper Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A portable radiation imaging apparatus, comprising:
a main body having wheels;
a supporting column standing on said main body, said supporting column defining a vertically extending axis, said supporting column defining a first height along the vertically extending axis;
a lifting member system including a first lifting member that moves up and down along said supporting column while holding a radiation irradiation element and a second lifting member that moves up and down along said first lifting member, said lifting member system defining an adjustable second height, said adjustable second height being greater than said first height;
a turntable that is fixed to a bottom end of the supporting column, said turntable being revolvable about said vertically extending axis, said turntable including a circular surface holding bearing installed underneath said supporting column, wherein said circular surface holding bearing supports said supporting column, wherein said supporting column revolves with said turntable around the vertically extending axis, wherein an external surface of said circular surface holding bearing has a first radius (R1) from a revolving center of said supporting column;
an idler element installed to a circumference of said surface holding bearing, wherein said idler element comprises a circular hole having a second radius (R2) that is larger than said first radius (R1) from said revolving center of said supporting column;
a first circular circumference of said idler element having a third radius (R3) from said revolving center of said supporting column that is larger than said second radius (R2);
a second circular circumference of said idler element having a fourth radius (R4) from said revolving center of said supporting column that is larger than said third radius (R3);
a revolving-side stopper that is connected with said turn table proximate said supporting column so that said revolving-side stopper revolves along with said supporting column, wherein said revolving-side stopper is installed at a first distance that is longer than said third radius (R3) and that is shorter than said fourth radius (R4) from said revolving center of said supporting column; and
a fixing-side stopper that is fixed to said main body at a second location at a second distance between longer than said third radius (R3) and shorter than said fourth radius (R4) from said revolving center of said supporting column.

2. The portable radiation imaging apparatus, according to claim 1, wherein:
said surface holding bearing is at least one bearing selected from a group consisting of a cross-roller bearing and a swing bearing.

3. The portable imaging apparatus, according to claim 1, wherein:
said lifting member is positioned above a top end of said supporting column when said lifting member is in-place in a climbing position.

* * * * *